United States Patent [19]
Bergeron, Jr.

[11] Patent Number: 5,973,113
[45] Date of Patent: *Oct. 26, 1999

[54] HYPUSINE REAGENT FOR PEPTIDE SYNTHESIS

[75] Inventor: Raymond J. Bergeron, Jr., Gainesville, Fla.

[73] Assignee: University of Florida Research Foundation, Inc., Gainesville, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/962,300

[22] Filed: Oct. 31, 1997

[51] Int. Cl.$^6$ .......................... C07K 1/00; C07C 229/00
[52] U.S. Cl. .................. 530/331; 530/333; 562/561; 562/562; 562/564
[58] Field of Search .................. 530/331, 333; 562/561–562, 564

[56] References Cited

PUBLICATIONS

Bergeron, R.J. et al., J. Org. Chem. vol. 58, No. 24 6804–6 (1993).

Bergeron, R.J. et al. J. Org. Chem vol. 62, No. 10 3285–90 (May 1997).

*Primary Examiner*—Bennett Celsa
*Attorney, Agent, or Firm*—Kerkam, Stowell, Kondracki & Clarke; Dennis P. Clarke

[57] ABSTRACT

A derivative of hypusine useful as a reagent for synthesizing peptides containing hypusine, as well as a method for synthesizing the same, the derivative having the formula:

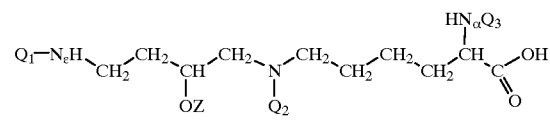

wherein:

$Q_1$ and $Q_2$ may be the same or different and are amino protective groups;

$Q_3$ is an amino protective group which is orthogonal to $Q_1$ and $Q_2$; and

Z is a hydroxy protective group.

25 Claims, 1 Drawing Sheet

α (a) (BOC)₂O, NaHCO₃; (b) H₂, Pd-C; (c) PhCHO, NaBH₃CN; (d) (S)•(+)-epichlorohydrin, MgSO₄; (e) KCN; (f) H₂, Pd-C, PtO₂; (g) CBZ-Cl, DIEA; (h) TFA, triethylsilane, CH₂Cl₂; (i) 3, 4-dihydro-2H-pyran; (j) FMOC-ONSu, Na₂CO₃.

HYPUSINE REAGENT FOR PEPTIDE SYNTHESIS

BACKGROUND OF THE INVENTION

1. Field of the Invention

The present invention relates to novel hypusine derivatives useful as reagents for synthesizing peptides containing hypusine.

2. Description of the Prior Art

Hypusine [$N_\epsilon$-(4-amino-2-hydroxybutyl)lysine], an unusual naturally occurring amino acid, having the structure:

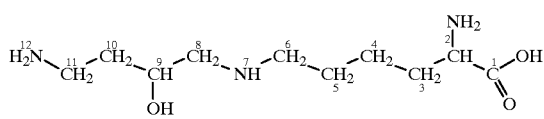

(A)

was first isolated from bovine brain extracts by Shiba et al in 1971 [*Biochim. Biophys. Acta.*, Vol. 244, pages 523–531 (1971)]. The molecule has two chiral centers, one at position 2 and one at position 9, each of which can be classified R or S by the Cahn-Ingold-Prelog method. The post-translational formation of the (2S, 9R) diastereomer:

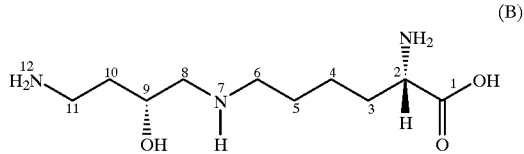

(B)

has been shown to occur on a precursor protein of the eukaryotic initiation factor "eIF-5A" (formerly called eIF-4D or IF-$M_2$BX; the nomenclature for initiation factors having been revised) [Cooper et al, *Proc. Natl. Acad. Sci. USA*, Vol. 80, pages 1854–1857 (1983); and Safer, *Eur. J. Biochem.*, Vol. 186, pages 1–3 (1989)]. This initiation factor 5A is unique in that it is the only known cellular protein that contains the amino acid hypusine (Hpu). In the mid-1970's, eIF-5A was shown to stimulate ribosomal subunit joining and to enhance 80 S-bound Met-t-RNA- reactivity with puromycin [Anderson et al, *FEBS Lett.*, Vol. 76, pages 1–10 (1977); and Kemper et al, *J. Biol. Chem.*, Vol. 251, pages 5551–5557 (1976)]. Later in 1983, Cooper et al, supra, suggested that a hypusine-modified protein serves as an important initiation factor in all growing eukaryotic cells. In 1986, Park et al [*J. Biol. Chem.*, Vol. 261, pages 14515–14519 (1986)] isolated the eIF-5A protein from human red blood cells and elucidated the amino acid sequence surrounding the single hypusine residue, as Thr-Gly-Hpu-His-Gly-His-Ala-Lys. Furthermore, and most interesting, because of the potential application to the control of HIV replication [Bevec et al, *J. Proc. Natl. Acad. Sci. USA*, Vol. 91, pages 10829–10833 (1994); and Ruhl et al, *J. Cell Biol.*, Vol. 123, pages 1309–1320 (1994)], the synthesis of eIF-5A analogues is of great therapeutic significance.

Since hypusine is specific to eIF-5A, antibodies derived from hypusine-containing peptides could be used to quantitate the levels of eIF-5A directly and with high specificity. Interest in developing an antibody assay of eIF-5A to investigate the physiological role of this important initiation factor prompted total synthesis of hypusine and its (2S, 9R)-diastereomer [Bergeron et al, *J. Org. Chem.*, Vol. 58, pages 6804–6806 (1993)]. The key step in the synthesis involved the $N_\epsilon$-alkylation of $N_\epsilon$-benzyl-$N_\alpha$-carbobenzoxy-(L)-lysine benzyl ester with (R)- or (S)-epichlorohydrin to give the respective (2S, 9R)- and (2S, 9S)-chlorohydrins. Subsequent displacement of the respective chlorides by cyanide ion provided the protected hypusine skeletons. The final step, hydrogenation over $PtO_2$ in AcOH, followed by neutralization and re-acidification, yielded the respective (2S, 9S)- and (2S, 9R)-hypusine dihydrochlorides. A comparison of the reported hypusine optical rotation with that of the synthetic (2S, 9R)-hypusine 1 confirmed the stereochemical integrity of both chiral centers throughout the synthesis.

Since there exists synthetic methodology for accessing hypusine itself, it would also be desirable to have a selectively-protected hypusine reagent which could be used to incorporate this unusual amino acid into selected peptides.

It is an object of the present invention to provide such novel hypusine reagents, as well as methods for their synthesis.

SUMMARY OF THE INVENTION

These and other objects are realized by the present invention, one embodiment of which comprises a derivative of hypusine useful as a reagent for synthesizing peptides containing hypusine, the derivative having the formula:

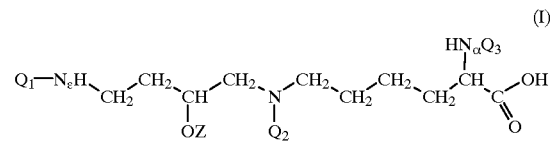

(I)

wherein:

$Q_1$ and $Q_2$ may be the same or different and are amino protective groups;

$Q_3$ is an amino protective group which is orthogonal to $Q_1$ and $Q_2$; and

Z is a hydroxy protective group.

An additional embodiment of the invention relates to a method for synthesizing a hypusine reagent as defined above comprising:

a. providing an ester of $N_\epsilon$-, $N_\alpha$-diprotected L-lysine, the ester having the formula:

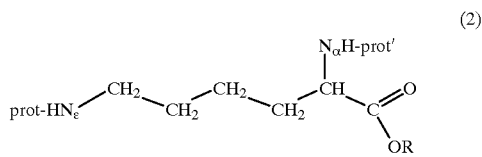

(2)

wherein prot and prot' are N-protective groups which are mutually orthogonal and R is the residue of an esterifying alcohol which is orthogonal with respect to prot and prot', b. removing prot from $N_\epsilon$ of (2) and converting the product to a compound of the formula:

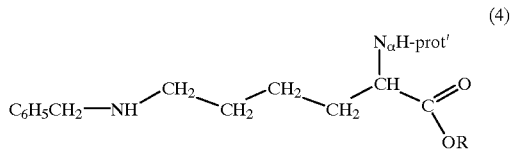
(4)

c. converting (4) to a chlorohydrin of the formula:

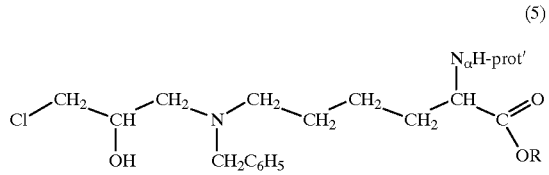
(5)

d. displacing the Cl group of (5) with CN to produce a nitrile of the formula:

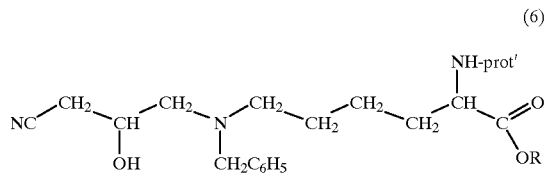
(6)

e. debenzylating the $N_\epsilon$ group and converting the CN group of (6) to an amine group to produce an amino alcohol of the formula:

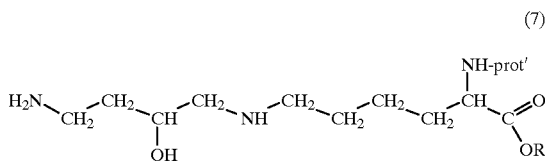
(7)

f. acylating the free amino groups of (7) to provide a di-N-protected $N_\alpha$-protected L-lysine ester of the formula:

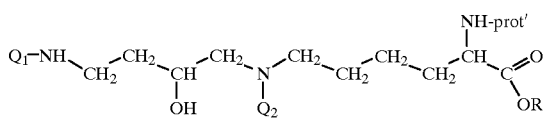
(8)

g. removing R and prot' from (8) to produce a compound of the formula:

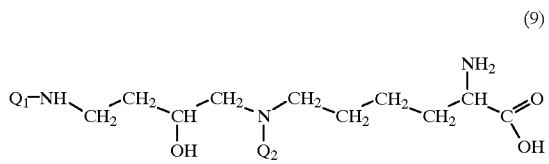
(9)

and h. acylating the free amino group and protecting the OH group to produce the hypusine derivative (I).

BRIEF DESCRIPTION OF THE DRAWING

Scheme 1 is a depiction of a reaction scheme for synthesizing the hypusine reagent of the invention.

DETAILED DESCRIPTION OF THE INVENTION

Figure 1:
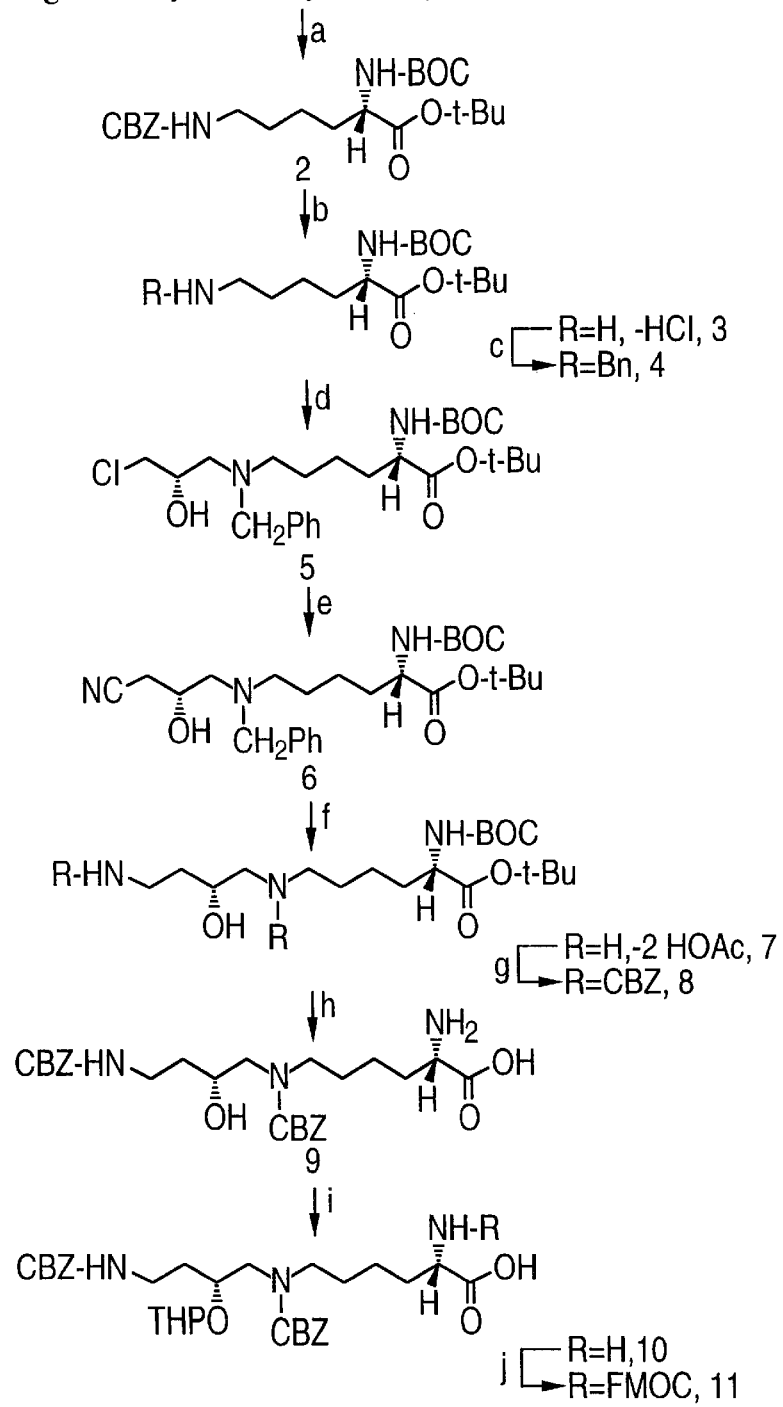

In the preceding and subsequent descriptions of the present specification, suitable examples and illustrations of the various definitions which the present invention includes within the scope thereof are explained in detail as follows.

The expression "amino protective group" as used herein is intended to designate groups ($Q_1$, $Q_2$ and $Q_3$) which are inserted in place of a hydrogen atom of an amino group or groups in order to protect the amino group(s) during synthesis.

Selection of a suitable amino protecting group will depend upon the reason for protection and the ultimate use of the protected product. When the protecting group is used solely for protection during synthesis, then a conventional amino protecting group may be employed. Appropriate amino protecting groups are known in the art and are described, for example, by Bodanszky in *Principles of Synthesis*, Springer-Verlag, N.Y. (1984); by Ives in U.S. Pat. No. 4,619,915; and in the various publications on peptide chemistry referred to in the latter. See also *Methoden der Organischen Chemie*, Houben-Weyl, Vol. 15, No. 1, for protecting groups and Vol. 15, No. 2, for methods of peptide synthesis. Representative amino protecting groups for synthetic use include acyl groups such as tert-butoxycarbonyl, benzyloxycarbonyl, fluorenylmethoxycarbonyl (FMOC), benzoyl, acetyl and the like. Yet other conventional amino protecting groups for use in synthesis are described in the literature [Bodanszky, supra, and Ives, supra].

The expression "hydroxyl protective group" as used herein is intended to designate a group (Z) which is inserted in place of a hydrogen atom of an OH group or groups in order to protect the OH group(s) during synthesis.

The preferred hydroxyl protective groups are the ethers, with the most preferred being the tetrahydropyranyl ether.

The term "orthogonal" when used herein to modify the term "protective group(s)" is intended to designate those protective groups in the molecule which are capable of being selectively removed from the molecule in the presence of other protective groups in the molecule without affecting the latter.

The various protecting groups for hydroxyl and amino functions discussed above can be substituted for the hydroxyl and amino functions in the instant amino acids/peptides (or their precursor molecules) by methods well known in the art. Methods for chemical removal of the protecting groups (when such are not to be retained in the pharmaceutically useful end product) are likewise well known to the skilled artisan. Typically, amine protecting groups are chemically removed by acidolysis (acid hydrolysis) or hydrogenation, depending on the particular protecting group employed. Hydroxyl and carboxyl protecting groups are typically removed chemically by acid or base hydrolysis. Protecting groups which are incorporated in the pharmaceutical end product must be amenable to hydrolytic or metabolic cleavage in vivo.

The hypusine reagents of the present invention are useful as synthons for accessing peptides, in particular, the eIF-5A pentapeptide sequence. Thus, peptides incorporating hypusine may be prepared by sequential addition to an amino acid or protected amino acid, or the addition of the reagent to an amino terminus free peptide. Thus, the reagent can be inserted directly into a dipeptide or larger fragment in the course of the peptide synthesis. At any point in the synthesis, the α-nitrogen protecting group of the hypusine reagent can be removed and the carboxylate group of an amino acid, a protected amino acid, or a carboxylate free peptide coupled to it. Methods for sequential addition of amino acids to form peptides, utilizing protecting groups where appropriate, are well known in the art. An excellent summary of such methods, including both solid phase synthesis and synthesis in solution, is contained in U.S. Pat. No. 4,530,920 (Nestor et al) which is relied upon and incorporated by reference herein in its entirety. See also *Solid Phase Peptide Synthesis*, second edition, John Morrow Stewart and Janis Dillaha Young, eds., Pierce Chemical Company, Rockford, Ill. (1984).

Peptides provided by the present invention can also be prepared by segment condensation methods described in the prior art [Bodanszky, supra, and *Methoden der Organischen Chemie*, supra].

Inspection of the structure of hypusine (A) reveals five potentially reactive centers: two primary amino and one secondary amino groups, a secondary hydroxyl group and a carboxyl group. In eIF-5A, the α-amino nitrogen (N2) required a protecting group which was orthogonal, i.e., removable under conditions different from those under which the groups masking N7 and N12 are removed, to those masking the other two potentially reactive amines (N7 and N12). Therefore, the N2 nitrogen was protected as, e.g., the N-FMOC derivative, while the N7 and N12 amines were protected as, e.g., the N-CBZ moieties. The 9-hydroxyl was masked as, e.g., a tetrahydropyranylether. This protection was necessary as the poorly reactive secondary hydroxyl was expected to cause difficulty with the anticipated N-acylating agents used in solid phase synthesis [Stewart, *The Peptides*, Vol. 3, page 170, Gross et al, eds., Academic Press, New York (1981)].

As shown in Scheme 1, the synthesis preferably begins with the t-butoxycarbonylation of $N_\epsilon$-CBZ-L-lysine t-Bu ester to give 2 in 98% yield [Tarbell et al, *Proc. Natl. Acad. Sci. USA*, Vol. 69, pages 730–732 (1972)].

The $N_\epsilon$-CBZ group of 2 was removed by hydrogenation over 10% Pd—C in ethanol and aqueous HCl to give 3 in 99% yield [Bergmann et al, *Ber. Dtsch.*, Chem. Abs., Vol. 65, pages 1192–1201 (1932)]. The $N_\epsilon$-benzyl-$N_\alpha$-BOC-L-lysine t-Bu ester 4 was synthesized from 3 by reductive amination of the liberated $N_\epsilon$ amine with benzaldehyde and sodium cyanoborohydride [Borch et al, *J. Am. Chem. Soc.*, Vol. 93, pages 2897–2904 (1971)].

The earlier synthesis of hypusine [Bergeron et al, supra] developed a chiral 4-amino-2-hydroxy butane synthon for accessing the parent molecule from an L-lysine derivative. In particular, this fragment made it possible to elaborate the $N_\epsilon$ benzyl group of a protected L-lysine into the N7–N12 structure of hypusine. In the synthesis of the present invention, this concept is further exploited. As shown in the reaction scheme depicted in Scheme 1, the subsequent $N_\epsilon$-alkylation of 4 with (S)-epichlorohydrin gave the (2S, 9S)-chlorohydrin (5). Displacement of the chloride in (5) by cyanide ion afforded the protected (2S, 9R)-hypusine skeleton (6). Debenzylation at N7 and conversion of the terminal nitrile in 6 was accomplished by hydrogenation to give the amino alcohol (7) as a diacetate. Acylation of the amino functions of amino alcohol (7) at N7 and N12 using CBZ groups as protecting groups provided di-CBZ-$N_\alpha$-t-BOC-(L)-lysine t-butyl ester (8). Selective removal of the t-butyl ester and $N_\alpha$-BOC protecting groups was accomplished with TFA and triethylsilane [Mehta et al, *Tetrahedron Lett.*, Vol. 33, pages 5441–5444 (1992)] to give the di-CBZ derivative 9. The secondary 9-hydroxyl function was protected as tetrahydropyranylether 10 [Bernady et al, *J. Org. Chem.*, Vol. 44, pages 1438–1447 (1979)] and subsequent acylation of the remaining $N_\alpha$-amine function with 9-fluorenylmethyl N-succinimidyl carbonate gave the hypusine reagent (11) with the desired protecting groups. Reagent (11) was converted to the dihydrochloride salt of (2S, 9R)-hypusine (1) to give identical $^1$H NMR and comparable optical rotation was cited in the art [Bergeron et al, supra] by removing the FMOC group with 4-aminomethyl-piperidine [Beyermann et al, *J. Org. Chem.*, Vol. 55, pages 721–728 (1990)] and de-protection of the remaining protecting groups following a method by Wang et al [*Int. J. Peptide Res.*, Vol. 40, pages 344–349 (1992)].

In a similar fashion, hypusine reagent molecules of differing stereochemistries may be obtained in a like manner employing starting materials of opposite stereochemistries such as (R)-epichlorohydrin.

The invention is illustrated by the following non-limiting examples which refer to a reaction scheme depicted in Scheme 1, wherein $^1$H NMR spectra were recorded at 300 MHz unless otherwise specified; $^{13}$C NMR spectra were recorded at 75 MHz unless otherwise specified; chemical shifts are given in parts per million downfield from an internal tetramethyl-silane or sodium 3-(trimethyl-silyl)-propionate standard; mass spectra were carried out on a Kratos MS 80RFA or a Finnigan 4516 MS instrument; optical rotations were run at 589 nm (the Na D-line) on a Perkin-Elmer 341 polarimeter, with c expressed as grams of compound per 100 ml; and melting points were uncorrected.

EXAMPLE 1

$N_\alpha$-BOC-$N_\epsilon$-CBZ-L-Lysine tert-Butyl Ester (2)

Sodium hydrogencarbonate (2.81 g, 33.47 mmol) in water (75 ml) was added to H-Lys(CBZ)—O—t-Bu hydrochloride (12.00 g, 32.18 mmol) in chloroform (100 ml) and the mixture was stirred at room temperature for 5 minutes under an $N_2$ atmosphere. Di-tert-butyl dicarbonate (7.02 g, 32.18 mmol) in chloroform (50 ml) was added, the mixture refluxed for 1.5 hours and allowed to cool to room temperature. The layers were separated, the aqueous layer extracted with chloroform (3×100 ml) and the combined organic layers dried over magnesium sulfate. Concentration in vacuo followed by flash chromatography (3:1 hexane:ethyl acetate) gave (2) (13.82 g, 98%) as a colorless oil. $^1$H NMR (CDCl$_3$) δ7.30 (s, 5H), 5.10 (s, 2H), 4.82 (m, 1H), 4.18 (m, 1H), 3.20 (m, 2H), 1.90–1.30 (m, 6H), 1.48 (s, 9H), 1.46 (s, 9H); $^{13}$C NMR (CD$_3$OD) δ173.8, 158.8, 158.1, 138.4, 129.4, 128.9, 128.7, 82.5, 80.4, 67.3, 55.7, 41.4, 32.4, 30.4, 28.7, 28.3, 24.0. HRMS m/z calcd. for $C_{23}H_{37}N_2O_6$ 437.2652, found 437.2643. Anal. calcd. for $C_{23}H_{36}N_2O_6$: C 63.8, H 8.31, N 6.42. Found: C 63.13, H 8.28, N 6.47. $[\alpha]^{27}_D$+5.0 (c=2.00, CHCl$_3$).

EXAMPLE 2

$N_\alpha$-BOC-L-Lysine tert-Butyl Ester Hydrochloride (3)

$N_\alpha$-BOC-$N_\epsilon$-CBZ-L-lysine tert-butyl ester (2) (34.51 g, 79.15 mmol) was dissolved in a mixture of 300 ml absolute EtOH and 1 N HCl (88 ml). Prior to the introduction of $H_2$ gas, 10% Pd—C (2.95 g) was added. After 7 hours, additional catalyst (1.0 g) was added. After 5 hours, the black suspension was filtered through a bed of Celite and washed with EtOH. The filtrate was concentrated and the residue dried under high vacuum to give the $N_\alpha$-BOC-L-lysine tert-butyl ester as its hydrochloride salt (3) (26.59 g, 99%). $^1$H NMR (CD$_3$OD) δ3.95 (dd, 1H, J=8.8, 5.0 Hz), 2.93 (t, 2H, J=7.7 Hz), 1.84–1.60 (m, 6H), 1.45 (s, 9H), 1.43 (s, 9H); $^{13}$C NMR (CD$_3$OD) δ173.5, 158.2, 82.7, 80.5, 79.5, 55.5, 40.6, 32.1, 28.7, 28.3, 23.9. HRMS m/z calcd. for $C_{15}H_{31}N_2O_4$ 303.2284, found 303.2272. $[\alpha]^{26}_D$ –10.1° (c=1.00, CH$_3$OH).

EXAMPLE 3

$N_\epsilon$-Benzyl-$N_\alpha$-BOC-L-Lysine tert-Butyl Ester (4)

$N_\alpha$-BOC-L-lysine t-butyl ester hydrochloride salt (3) (25.97 g, 76.64 mmol) was dissolved in CHCl$_3$ (300 ml) and washed with saturated aqueous Na$_2$CO$_3$ solution (2×100 ml). The organic layer was separated, dried (MgSO$_4$), filtered and concentrated. The resultant oil (the free amine) was combined with benzaldehyde (10.42 g, 98.13 mmol), EtOH (150 ml) and activated 3 Å molecular sieves (46.0 g). The mixture was stirred under N$_2$ for 6 hours. Sodium cyanoborohydride (2.41 g, 38.4 mmol) was added and the mixture was stirred overnight at room temperature. The brown mixture was filtered and the filtrate acidified to pH 2 with 1 N HCl (110 ml). The yellow solution was concentrated to dryness, dissolved in CHCl$_3$, washed with saturated Na$_2$CO$_3$ solution and water. The organic layer was separated, dried (MgSO$_4$) and concentrated. Flash column chromatography (10% EtOH/CHCl$_3$, R$_f$=0.30) afforded the $N_\epsilon$-benzyl-$N_\alpha$-BOC-L-lysine t-butyl ester (4) (16.16 g, 54%) as a colorless oil. $^1$H NMR (CD$_3$OD) δ7.34–7.20 (m, 5H), 3.91 (dd, 1H, J=9.0, 5.1 Hz), 3.72 (s, 2H), 2.58 (t, 2H, J=7.2 Hz), 1.82–1.30 (m, 6H), 1.45 (s, 9H), 1.43 (s, 9H); $^{13}$C NMR (CDCl$_3$) δ171.9, 155.3, 140.1, 128.3, 128.1, 126.9, 81.6, 79.5, 53.9, 48.9, 32.7, 29.5, 28.3, 27.9, 22.9. HRMS m/z calcd. for $C_{22}H_{36}N_2O_4$ 392.2675, found 392.2676. Anal. calcd. for $C_{22}H_{35}N_2O_4$: C 67.32, H 9.24, N 7.14. Found: C 67.40, H 9.28, N 7.16. $[\alpha]^{25}_D$+6.9° (c=1.00, CDCl$_3$).

EXAMPLE 4

(2S, 9S)-7-Benzyl-2-[(tert-butoxycarbonyl)amino]-10-chloro-9-hydroxy-7-azadecanoic Acid, tert-Butyl Ester (5)

A mixture of $N_\epsilon$-benzyl-$N_\alpha$-BOC-L-lysine t-butyl ester (4) (16.0 g, 40.76 mmol), CH$_3$OH (40 ml), (S)-(+)-epichlorohydrin (4.17 g, 45.0 mmol) and anhydrous MgSO$_4$ (5.33 g. 44.28 mmol) was stirred under N$_2$ for three days. The solids were filtered off and washed with CH$_3$OH. The filtrate was concentrated at room temperature to give a yellow oil. The resulting oil was purified by flash chromatography on silica gel (66% hexane/ethyl acetate) to give 13.23 g of (5) (77%) as a colorless oil. $^1$H NMR (C$_6$D$_6$) δ7.18 (m, 5H), 5.00 (br d, 1H), 4.40 (m, 1H), 3.62 (m, 1H), 3.40–3.10 (m, 4H), 2.20–2.00 (m, 4H), 1.63 (m, 1H), 1.40 (s, 9H), 1.31 (s, 9H), 1.20 (m, 2H). $^{13}$C NMR (C$_6$D$_6$) δ171.7, 155.2, 138.8, 128.8, 127.9, 127.0, 80.8, 78.8, 67.7, 58.8, 57.2, 53.9, 53.7, 47.3, 32.5, 28.0, 27.5, 26.3, 22.8. HRMS m/z calcd. for $C_{25}H_{42}ClN_2O_5$ 485.2782, found 485.2775. $[\alpha]^{25}_D$+5.3° (c=1.00, CHCl$_3$).

EXAMPLE 5

(2S, 9R)-7-Benzyl-2-[(tert-butoxycarbonyl)amino]-10-cyano-9-hydroxy-7-azadecanoic Acid tert-Butyl Ester (6)

A mixture of (5) (6.99 g, 14.4 mmol), dry KCN (9.38 g, 144 mmol) and 18-crown-6 (0.76 g, 2.88 mmol) in 275 ml of dry acetonitrile was stirred at 45° C. for 5 days. It should be noted that heating this mixture to reflux causes significant decomposition. The reaction mixture was cooled, filtered and concentrated. Flash column chromatography on silica gel (25% ethyl acetate/hexane) gave the (2S, 9R)-nitrile (6) as a colorless oil (4.82 g, 70%). $^1$H NMR (CD$_3$OD) δ7.34–7.18 (m, 5H), 3.97–3.83 (m, 2H), 3.67 (dd, 1H, J=13.4, 2.6 Hz), 3.54 (dd, 1H, J=13.4, 4.0 Hz), 2.72–2.40 (m, 6H), 1.80–1.50 (m, 4H), 1.45 (s, 9H), 1.44 (s, 9H), 1.40–1.30 (m, 2H). $^{13}$C NMR (CDCl$_3$) δ171.8, 155.3, 138.1, 128.8, 128.4, 127.3, 117.1, 81.6, 79.5, 63.6, 58.8, 54.0, 32.6, 28.2, 27.9, 22.1. HRMS m/z calcd. for $C_{26}H_{42}N_3O_5$ 476.3124, found 476.3121. Anal. calcd. for $C_{26}H_{41}N_3O_5$: C 65.66, H 8.69, N 8.83. Found: C 65.71, H 8.67, N 8.80. $[\alpha]^{25}_D$+4.7° (c=1.00, CHCl$_3$).

EXAMPLE 6

(2S, 9R)-2-[(tert-Butoxycarbonyl)amino]-11-amino-9-hydroxy-7-azaundecanoic Acid tert-Butyl Ester, Diacetate Salt (7)

The $N_\epsilon$ benzyl nitrile (6) (4.80 g, 10.7 mmol) was dissolved in glacial acetic acid (100 ml); 10% Pd—C (0.50 g) and PtO$_2$ (1.00 g) were added; and hydrogen gas was introduced. The reaction was complete after 6 hours, and the catalyst was filtered through a bed of Celite and washed with acetic acid. The filtrate was concentrated in vacuo. Azeotropic removal of the acetic acid with toluene gave (7) as a colorless oil (5.10 g, 99%) $^1$H NMR (500 MHz) (CD$_3$OD) δ4.02–3.94 (m, 2H), 3.14–2.86 (m, 6H), 1.94 (s, 6H), 1.87–1.58 (m, 8H), 1.46 (s, 9H), 1.44 (s, 9H). $^{13}$C NMR (CD$_3$OD) δ169.6, 156.54, 85.3, 70.2, 62.6, 56.6, 54.2, 53.9, 34.0, 31.1, 28.2, 26.3, 23.2. HRMS m/z calcd. for $C_{19}H_{40}N_3O_5$ 390.2968, found 390.2977. $[\alpha]^{25}_D$+0.6° (c=1.00, CH$_3$OH).

EXAMPLE 7

(2S, 9R)-11-[(Benzyloxycarbonyl)amino]-2-[(tert-butoxycarbonyl)amino]-9-hydroxy-7-carbobenzyloxy-7-azaundecanoic Acid tert-Butyl Ester (8)

A solution of (7) (1.17 g, 2.30 mmol) in CHCl$_3$ (100 ml) was washed with saturated Na$_2$CO$_3$ solution. The aqueous layer was extracted with CHCl$_3$ (3×100 ml) and the combined organic layers were dried over Na$_2$SO$_4$ and concentrated in vacuo. A solution of the resultant oil (the free amine, 0.85 g, 2.18 mmol) in CH$_2$Cl$_2$ (60 ml) was cooled to 0° C. and treated with diisopropylethylamine (0.59 g, 4.57 mmol) and benzyl chloroformate (0.79 g, 4.60 mmol). The reaction mixture was stirred overnight at room temperature, concentrated to dryness and purified by flash chromatography (50% ethyl acetate/hexane) to give (8) (790 mg, 55%) as a colorless oil. $^1$H NMR (CDCl$_3$) δ7.23 (m, 10H), 5.45 (m, 1H), 5.08 (s, 2H), 5.04 (s, 2H), 4.10 (m, 1H), 3.80 (m, 1H), 3.40 (m, 1H), 3.23 (m, 5H), 1.80–1.43 (m, 6H), 1.41 (s, 18H), 1.23 (m, 2H); $^{13}$C NMR (CDCl$_3$) δ171.8, 157.5, 156.9, 155.3, 136.4, 128.4, 128.3, 127.9, 127.7, 81.6, 79.5, 69.2, 67.2, 66.5, 53.7, 48.5, 37.7, 34.8, 32.5, 28.2, 27.9, 22.3. HRMS m/z calcd. for $C_{35}H_{52}N_3O_9$ 658.3703, found 658.3774. $[\alpha]^{24}_D$+4.6° (c=0.50, CHCl$_3$).

EXAMPLE 8

(2S, 9R)-11-[(Benzyloxycarbonyl)amino]-7-(carbobenzyloxy)-9-hydroxy-7-azaundecanoic Acid (9)

The ester (8) (500 mg, 0.76 mmol) was dissolved in a pre-made mixture of trifluoroacetic acid (1.12 g, 9.90 mmol), CH$_2$Cl$_2$ (2.05 g, 24.0 mmol) and triethylsilane (220 mg, 1.9 mmol) and stirred at room temperature for 20 hours. The reaction mixture was concentrated to dryness and stirred again in the pre-made mixture as described above for an additional 6 hours. The reaction mixture was concentrated and the resultant oil dissolved in 1.0 ml water and adjusted to pH 8 with saturated NaHCO$_3$ solution. The solution was concentrated and purified by chromatography on a C-18 column (55% acetone/water) to give 300 mg (78%) of (9) as a colorless oil. $^1$H NMR (CD$_3$OD) $\delta$7.40–7.25 (m, 10H), 5.11 (s, 2H), 5.06 (s, 2H), 3.82 (m, 1H), 3.55 (m, 1H), 3.40–3.10 (m, 6H), 1.95–1.30 (m, 8H). HRMS m/z calcd. for C$_{26}$H$_{36}$N$_3$O$_7$ 502.2553, found 502.2531. [α]$^{24}_D$+4.2° (c=1.00, CH$_3$OH).

EXAMPLE 9

(2S, 9R)-2-Amino-11-[(Benzyloxycarbonyl)amino]-7-(carbobenzyloxy)-9-(tetrahydropyran-2-yloxy)-7-azaundecanoic Acid (10)

Trifluoroacetic acid (115 mg, 1.01 mmol) was added to a solution of (9) (265 mg, 0.53 mmol) in CHCl$_3$ (5 ml). The solution was concentrated in vacuo. The resultant oil was dissolved in dry CH$_2$Cl$_2$ (15 ml) and 3,4-dihydro-2H-pyran (51 mg, 55 μl, 0.61 mmol) was added at room temperature. The reaction progress was monitored by TLC and three additional portions of 3,4-dihydro-2H-pyran (51 mg each) were added over the next 7 hours. The reaction mixture was stirred for an additional 12 hours and concentrated in vacuo. The oil was dissolved in water and methanol (1:1, 4 ml) and adjusted to pH 7 with saturated NaHCO$_3$ solution. The solution was concentrated and the crude oil purified by chromatography on a C-18 column (55% acetone/water) to give 210 mg (68%) of (10) as a colorless oil and 20 mg (8%) recovered starting material (9). $^1$H NMR (CD$_3$OD) $\delta$7.40–7.22 (m, 10H), 5.10 (m, 2H), 5.04 (s, 2H), 4.62–4.32 (m, 1H), 4.02–3.68 (m, 2H), 3.50 (m, 1H), 3.44–3.06 (m, 7H), 1.98–1.28 (m, 14H); $^{13}$C NMR (CD$_3$OD) $\delta$174.3, 158.7, 158.1, 138.5, 129.7, 129.6, 129.5, 129.3, 129.0, 128.8, 101.7, 100.1, 74.9, 68.3, 67.4, 65.3, 56.2, 48.4, 38.2, 34.3, 32.6, 32.1, 28.5, 26.4, 23.6, 21.8, 21.2. HRMS m/z calcd. for C$_{31}$H$_{43}$N$_2$O$_8$ 586.3128, found 586.3118. [α]$^{24}_D$+ 4.0° (c=0.25, CH$_3$OH).

EXAMPLE 10

Sodium (2S, 9R)-11-[(Benzyloxycarbonyl)amino]-7-(carbobenzyloxy)-2-[(9-fluorenylmethoxycarbonyl)amino]-9-(tetrahydropyran-2-yloxy)-7-azaundecanoic Acid (11)

A solution of 9-fluorenylmethyl N-succinimidyl carbonate (181 mg, 0.53 mmol) in DMF (2.5 ml) was added to a solution of (10) (210 mg, 0.36 mmol) in 9% Na$_2$CO$_3$ (0.836 ml, 0.72 mmol) at 0° C. and stirred overnight at room temperature. The pH was adjusted to 7 with 0.1 N HCl. The mixture was concentrated to an oil and purified by flash chromatography (90% CHCl$_3$/MeOH) to give (11) (239 mg, 83%) as a colorless oil. $^1$H NMR (CDCl$_3$) $\delta$7.78 (m, 2H), 7.60 (m, 2H), 7.30 (m, 14H), 5.72 (m, 2H), 5.18 (s, 2H), 5.16 (s, 2H), 4.60 (m, 1H), 4.52–4.22 (m, 3H), 4.20 (m, 1H), 4.00–3.72 (m, 3H), 3.50–3.10 (m, 6H), 2.00–1.22 (m, 14H); $^{13}$C NMR (150 MHz) (CDCl$_3$) $\delta$174.6, 156.7, 156.4, 143.9, 143.8, 141.3, 136.8, 136.5, 128.5, 128.5, 128.1, 128.0, 127.9, 127.7, 127.1, 125.1, 124.9, 120.0, 100.7, 73.5, 67.4, 67.2, 66.6, 53.5, 48.4, 47.2, 32.9, 32.0, 31.5, 30.8, 28.0, 27.3, 25.2, 22.0, 21.1, 19.8. HRMS m/z calcd. for C$_{46}$H$_{53}$N$_3$O$_{10}$Na 830.3629, found 830.3661. Anal. calcd. for C$_{46}$H$_{53}$N$_3$O$_{10}$: C 68.38, H 6.61, N 5.20. Found: C 68.55, H 6.63, N 5.26. [α]$^{26}_D$+3.4° (c=1.00, CHCl$_3$).

I claim:

1. A derivative of hypusine useful as a reagent for synthesizing peptides containing hypusine, said derivative having the formula:

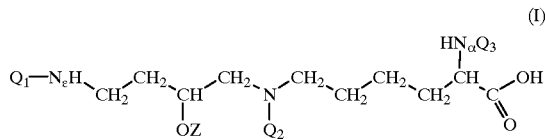

(I)

wherein:
Q$_1$ and Q$_2$ may be the same or different and are amino protective groups;
Q$_3$ is an amino protective group which is orthogonal to Q$_1$ and Q$_2$; and
Z is a hydroxy protective group.

2. A derivative of claim 1 wherein Q$_1$ and Q$_2$ are the same.

3. A derivative of claim 2 wherein Q$_1$ and Q$_2$ are benzylcarboxy.

4. A derivative of claim 1 wherein Q$_3$ is fluorenylmethoxycarbonyl.

5. A derivative of claim 1 wherein Z is tetrahydropyranyl.

6. A derivative of claim 1 wherein Q$_1$ and Q$_2$ are benzylcarboxy, Q$_3$ is fluorenylmethoxycarbonyl and Z is tetrahydropyranyl.

7. A method of synthesizing a hypusine derivative of claim 1 comprising:
a. providing an ester of N$_\epsilon$-, N$_\alpha$-diprotected L-lysine, said ester having the formula:

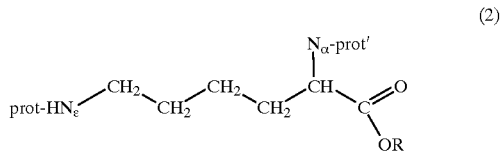

(2)

wherein prot and prot' are mutually orthogonal amino-protective groups and R is the residue of an esterifying alcohol which is orthogonal with respect to prot and prot',
b. removing prot from N$_\epsilon$ of (2) and converting the product to a compound of the formula:

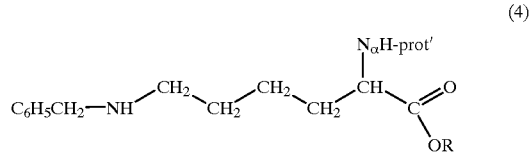

(4)

c. converting (4) to a chlorohydrin of the formula:

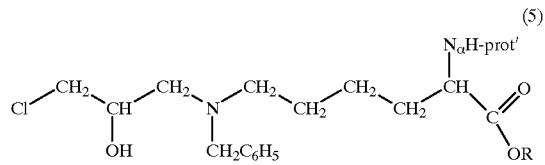

(5)

d. displacing the Cl group of (5) with CN to produce a nitrile of the formula:

(6)

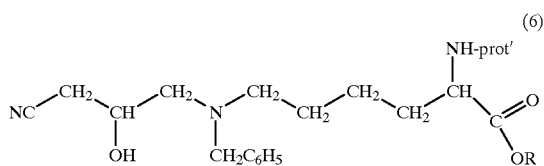

e. debenzylating the $N_\epsilon$ group and converting the CN group of (6) to an amine group to produce an amino alcohol of the formula:

(7)

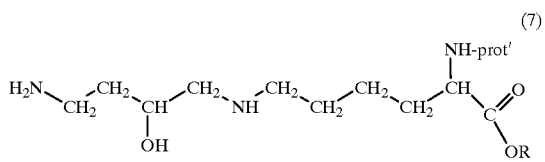

f. acylating the free amino groups of (7) to provide a di-N-protected $N_\alpha$-protected L-lysine ester of the formula:

(8)

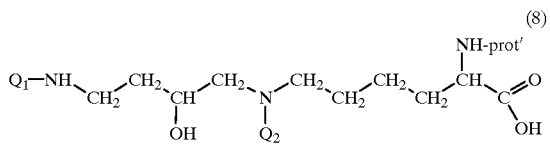

g. removing R and prot' of (8) to produce a compound of the formula:

(9)

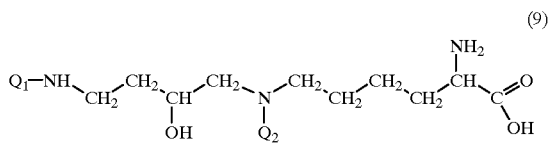

and h. acylating the free amino group and protecting the OH group to produce the hypusine derivative (I) of claim 1.

8. The method of claim 7 wherein ester (2) is provided by esterifying the $N_\epsilon$-, $N_\alpha$-diprotected L-lysine.

9. The method of claim 8 wherein prot is benzylcarboxy.

10. The method of claim 8 wherein prot' is BOC.

11. The method of claim 8 wherein R is t-butyl.

12. The method of claim 7 wherein prot is removed from (2) by hydrogenation and the resulting deprotected amine is converted to (4) by reductive amination of the free amine group with benzaldehyde.

13. The method of claim 12 wherein said reductive amination is effected in the presence of $NaBH_3CN$.

14. The method of claim 7 wherein (4) is converted to said (2S, 9S) chlorohydrin (5) by $N_\epsilon$-alkylation of (4) with (S)-epichlorohydrin.

15. The method of claim 7 wherein said alkylation with (S)-epichlorohydrin is conducted at substantially room temperature.

16. The method of claim 7 wherein said Cl group of (5) is displaced with CN by reaction of (5) with a cyanide reactive therewith.

17. The method of claim 16 wherein said cyanide is an alkali metal cyanide.

18. The method of claim 7 wherein (5) is $N_\epsilon$-debenzylated and the CN group thereof converted to an amino group by catalytic hydrogenation.

19. The method of claim 18 wherein said hydrogenation is conducted in the presence of a mixture of palladium-C and $PtO_2$.

20. The method of claim 7 wherein the free amino groups of (7) are acylated with a reactive benzylcarboxylic acid derivative to produce (8) wherein $Q_1$ and $Q_2$ are each benzylcarboxy groups.

21. The method of claim 20 wherein said reactive benzylcarboxylic acid is benzyl chloroformate.

22. The method of claim 7 wherein R and prot' are removed by reaction with trifluoroacetic acid.

23. The method of claim 22 wherein said reaction with trifluoroacetic acid is conducted in the presence of triethylsilane.

24. The method of claim 7 wherein the free amino group of (9) is acylated with 9-fluorenylmethyl-N-succinimidyl carbonate to produce a hypusine reagent wherein $Q_3$ is fluorenylmethoxycarbonyl.

25. The method of claim 7 wherein the hydroxy group of (9) is etherified with 3,4-dihydro-2H-pyran.

* * * * *

UNITED STATES PATENT AND TRADEMARK OFFICE
CERTIFICATE OF CORRECTION

PATENT NO. : 5,973,113
DATED : October 26, 1999
INVENTOR(S) : Raymond J. BERGERON, Jr.

It is certified that error appears in the above-indentified patent and that said Letters Patent is hereby corrected as shown below:

Column 11, line 29, the "OH" in formula (8), second occurrence, should read --OR--.

Signed and Sealed this

Sixth Day of March, 2001

Attest:

Attesting Officer

NICHOLAS P. GODICI

Acting Director of the United States Patent and Trademark Office